(12) United States Patent
Clements et al.

(10) Patent No.: US 6,863,657 B1
(45) Date of Patent: Mar. 8, 2005

(54) DEVICE FOR SUPPORTING PATELLAR TENDON

(76) Inventors: Keith Clements, 1701 Meadow Chase La., Knoxville, TN (US) 37931; Allison Leigh Wedding Lay, 8007 Gate Stone La., Powell, TN (US) 37849; Peggy Sue Ensley, 320 Big Ridge Park Rd., Maynardville, TN (US) 37807

( * ) Notice: Subject to any disclaimer, the term of this patent is extended or adjusted under 35 U.S.C. 154(b) by 0 days.

(21) Appl. No.: 10/726,088

(22) Filed: Dec. 2, 2003

(51) Int. Cl.[7] .............................. A61F 5/00; A61F 13/00
(52) U.S. Cl. ............................ 602/26; 602/23; 602/61; 602/62
(58) Field of Search .............................. 602/20, 23, 26, 602/19, 21, 60, 62; 128/876

(56) References Cited

U.S. PATENT DOCUMENTS

| D251,682 S | 4/1979 | Levine |
|---|---|---|
| 4,334,528 A | 6/1982 | Gauvry |
| 4,466,428 A | 8/1984 | McCoy |
| 4,532,921 A * | 8/1985 | von Torklus et al. ......... 602/26 |
| 5,556,374 A | 9/1996 | Grace et al. |
| 5,865,782 A | 2/1999 | Fareed |
| 6,485,448 B2 | 11/2002 | Lamping et al. |

OTHER PUBLICATIONS

Knee Support Products (p. 11) www.microbiomedics.com.
Sports Health® Knee Support www.esportshealth.com.

* cited by examiner

*Primary Examiner*—Kim M. Lewis
(74) *Attorney, Agent, or Firm*—Luedeka, Neely & Graham PC

(57) ABSTRACT

A device for providing support, compression, and warmth to the patellar tendon of a knee, the device including an elastic sleeve, a compressible tubular member secured along the circumferential length of the sleeve; first and second straps secured adjacent the exterior of the sleeve and generally diametrically across the sleeve from the tubular member; and first and second strap closure members for securing the straps in a tensioned state.

4 Claims, 6 Drawing Sheets

DEVICE FOR SUPPORTING PATELLAR TENDON

FIELD OF THE INVENTION

This invention relates generally to devices for treating knee pain. More particularly, the invention relates to devices for providing compression, support, and warmth to the patellar tendon, and for changing the distribution of tensile forces on a musculotendinous junction at or near its bony insertion.

BACKGROUND AND SUMMARY OF THE INVENTION

The patellar tendon connects the patella (the kneecap) to the shin bone. Patellar tendinitis is a painful condition associated with inflammation or irritation of the patellar tendon and surrounding tissue. Devices for changing the distribution of tensile forces on the patellar tendon and which provide compression, support, and warmth to the patellar tendon are often used to treat patellar tendonitis. The present invention is directed to a device of improved application and design for re-distributing tensile forces along the patellar tendon, in addition to providing support, compression, and warmth to the patellar tendon.

In a preferred embodiment, the device includes an elastic sleeve, a compressible tubular member secured along a circumferential length of the sleeve, first and second straps secured adjacent the exterior of the sleeve and generally diametrically across the sleeve from the tubular member, and first and second strap closure members for securing the straps in a tensioned state.

In another embodiment, the device includes an elastic sleeve having a circumferential length and opposite interior and exterior surfaces; a compressible tubular member having first and second opposite ends and secured along the circumferential length of the sleeve; and first and second straps secured adjacent the exterior of the sleeve and generally diametrically across the sleeve from the tubular member.

The first strap includes a hook surface and an adjacent loop surface and is secured adjacent the exterior surface of the sleeve at a first attachment point. The second strap includes a hook surface and an adjacent loop surface and is secured adjacent the exterior surface of the sleeve at a second attachment point located generally adjacent to the first attachment point so that the first and second straps may be positioned to extend in generally opposite directions around the exterior circumference of the sleeve.

A first strap closure member is secured adjacent the exterior surface of the sleeve and positioned between the first attachment point and the first end of the tubular member. A second strap closure member is secured adjacent the exterior surface of the sleeve and positioned between the second attachment point and the second end of the tubular member.

The device is positionable on the knee so that the tubular member is generally oriented across a front portion of the knee adjacent the patellar tendon and the device may be tensioned to provide compression and support to the patellar tendon by (1) exerting a first force on the first strap and passing the first strap through the first strap closure member and folding the first strap back to secure the hook material and the loop material of the first strap together to maintain application of the first force and (2) exerting a second force on the second strap and passing the second strap through the second strap closure member and folding the second strap back to secure the hook material and the loop material of the second strap together to maintain application of the second force.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

DETAILED DESCRIPTION

Figure 1:
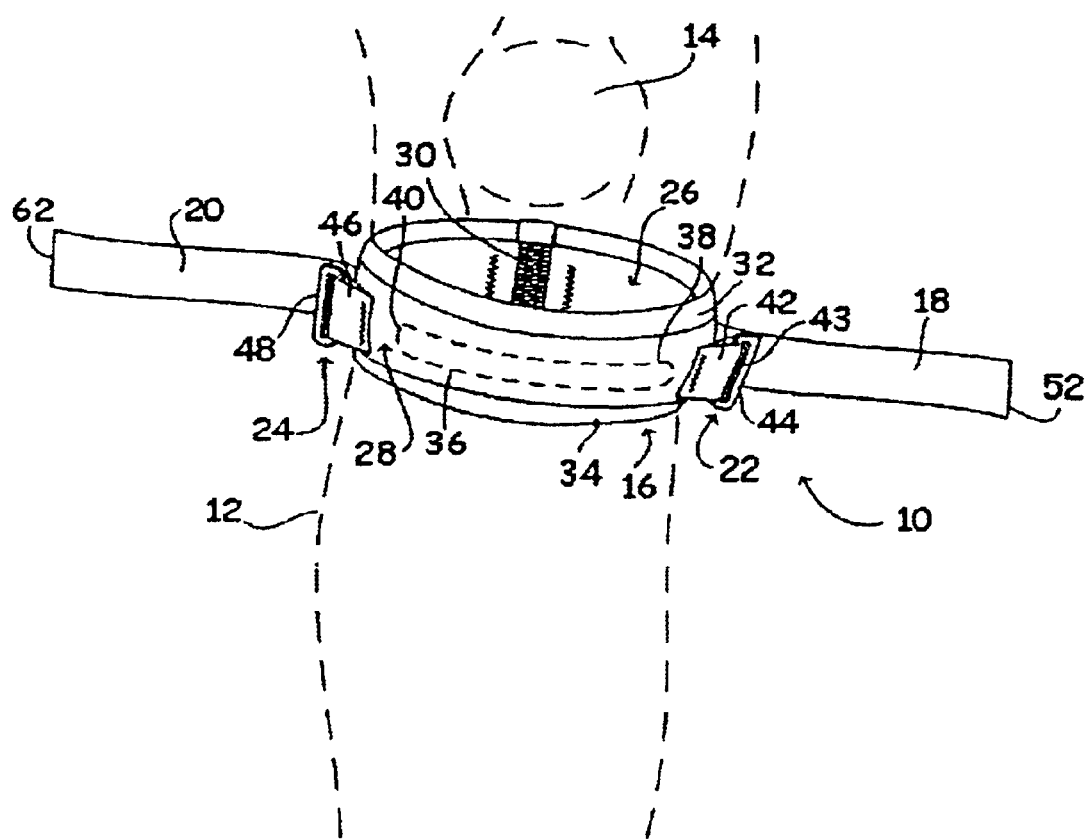
FIG. 1 is a frontal perspective view of a patellar tendon support device according to a preferred embodiment of the invention.
Figure 2:
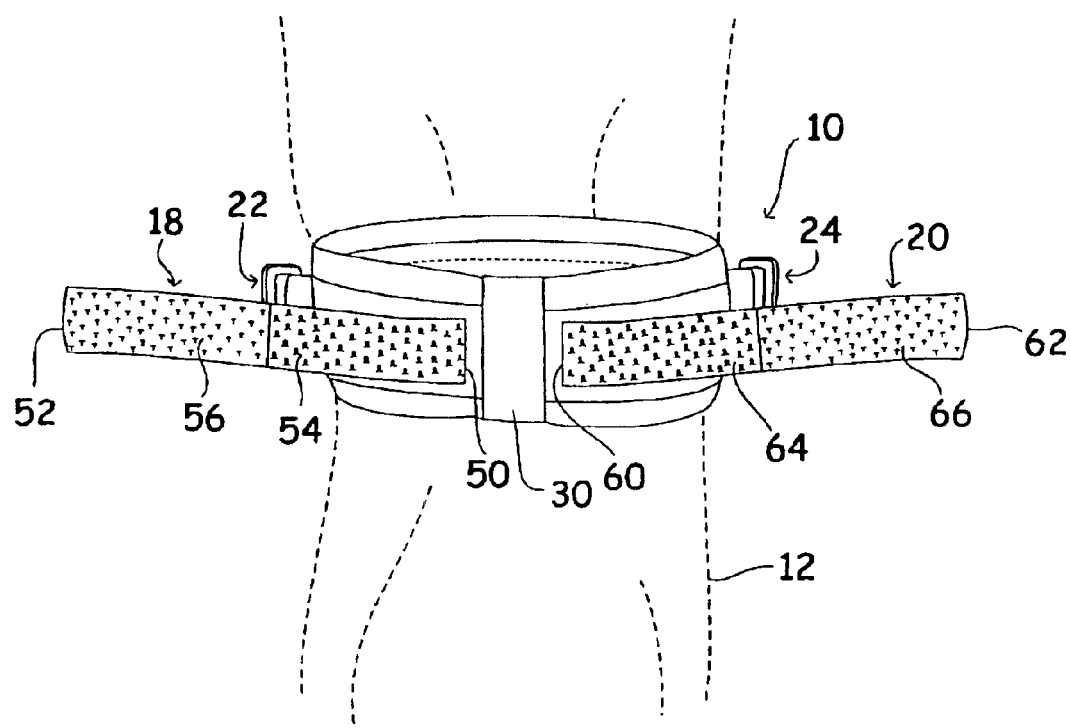
FIG. 2 is a rear perspective view of the device of FIG. 1.

With reference to FIGS. 1 and 2, the invention relates to a device 10 for providing support, compression, and warmth to the patellar tendon. The device 10 is shown for reference positioned on leg 12 of a user below patella or kneecap 14 (all shown in phantom), it being understood that the patellar tendon connects the inferior aspect of the kneecap to the tibia.

The device 10 includes an elastic sleeve 16, a pair of straps 18 and 20, and a pair of strap closure members 22 and 24. The sleeve 16 is a continuous closed loop made of an elastic fabric material, such as nylon, spandex or the like, and having an interior surface 26 and an exterior surface 28. The sleeve 16 may be made from a length of fabric material having the ends sewn together as by stitches to form seam 30, with the portion adjacent the seam 30 preferably contoured to fit comfortably below the popliteal region (back of the knee).

Upper cuff 32 and lower cuff 34 are preferably provided at the edges of the sleeve 16 for comfort and aesthetics. The cuffs 32 and 34 are preferably made of an elastic fabric material and each have a circumference slightly smaller than the circumference of the sleeve 16. In this regard, the sleeve 16 is preferably provided in a number of sizes for use by persons having various leg dimensions corresponding to the following knee circumferences as measured just below the kneecap, with the sleeve circumference being obtained with the sleeve in a relaxed or unstretched state:

| sleeve circumference (in) | knee circumference (in) |
| --- | --- |
| 8 | 11–12 |
| 9 | 12–13 |
| 10 | 13–14 |
| 11 | 14–15 |
| 12 | 15–16 |
| 13 | 16–17 |

A compressible tubular member 36 having opposite ends 38 and 40 is secured to the sleeve 16 adjacent the interior surface 26. The tubular member 36 may preferably be a rubber latex tube having a length of from about 3 to about 6 inches. A preferred tube preferably has an inner diameter of about 3/16 inch and an outer diameter of about 3/8 inch. The tubular member 36 is secured adjacent the interior surface 26 as by having a section of the fabric material used to provide the sleeve 16 secured, as by sewing, to the surface 26 to provide a pocket for receiving the tubular member 36. The tubular member 36 may be secured adjacent the surface 26 in other ways, as by stitches, fasteners, adhesives and the like. The midpoint of the tubular member 36 is preferably opposite the seam 30. As described in more detail below, the device 10 is positioned on the leg of the user so that the tubular member 36 is below the front of the kneecap and positioned at a location to lay across the location of the patellar tendon.

The strap closure members 22 and 24 are preferably secured to the exterior surface 28 of the sleeve 16 at locations proximate the locations of the ends 38 and 40 of the tubular member 36. The closure member 22 preferably includes a length of fabric material having the ends thereof attached, as by stitches, to the surface 28 to form a loop 42 of fabric material, with a D-ring 44 secured thereto as by the loop 42 passing through an aperture 43 in the D-ring 44. Likewise, the closure member 24 includes a loop 46 and a D-ring 48 secured thereto.

The strap 18 includes opposite ends 50 and 52, preferably with an overall length of from about 5 to about 7 inches and a width of from about 1/2 to about 3/4 inch. The end 50 is preferably attached closely adjacent the seam 30 to the exterior surface 28, as by sewing. The strap 18 may preferably be made of a nylon fabric material and includes a loop material 54 and hook material 56 secured to the surface thereof disposed as seen in FIG. 2 to face away from the surface 28. The loop material 54 and the hook material 56 each have a length of about half of the length of the strap 18. The strap 20 is preferably substantially identical to the strap 18 and is attached closely adjacent the opposite side of the seam 30. The strap 20 preferably includes opposite ends 60 and 62, and loop material 64 and hook material 66.

Figure 3:
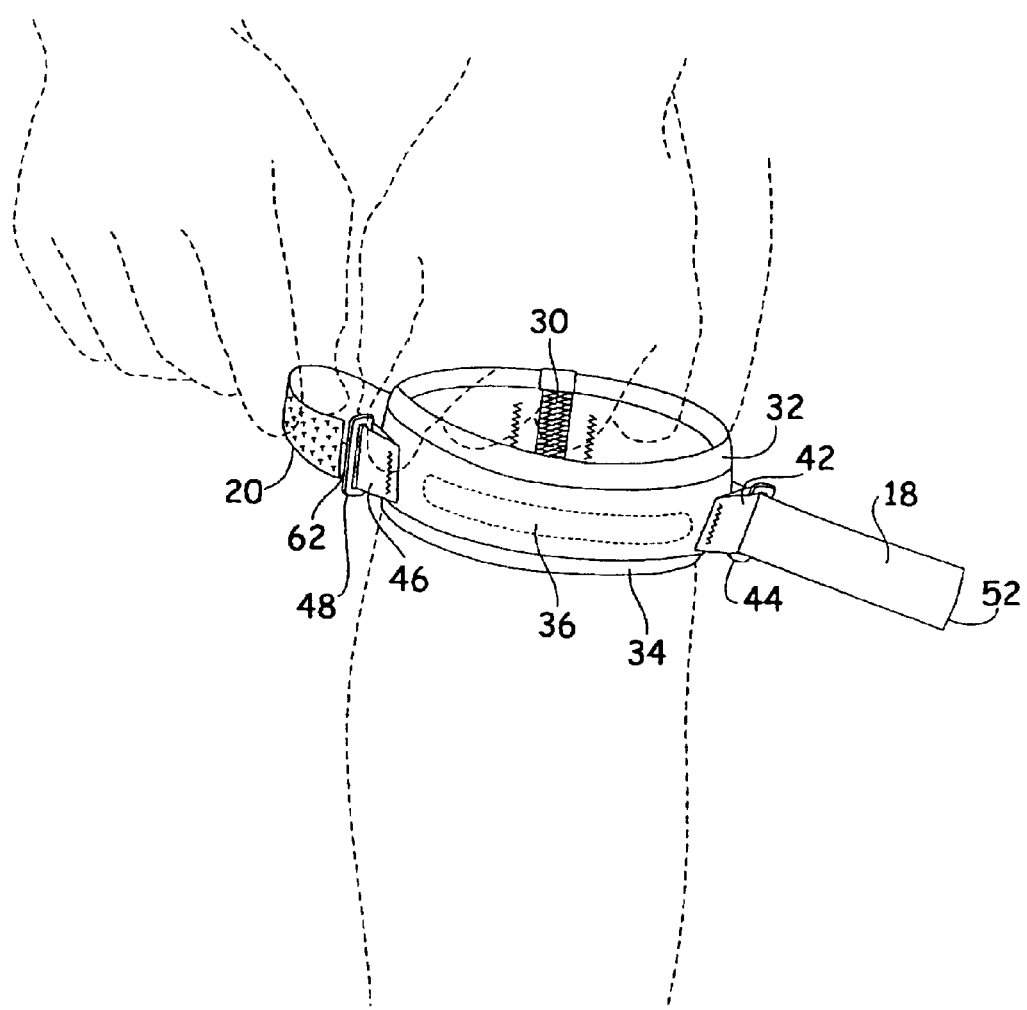
FIGS. 3–6 show preferred steps in the installation of the device of FIG. 1 on a user to re-distribute tensile forces along the patellar tendon, while providing support, compression, and warmth to the patellar tendon.

The device 10 is preferably positioned on the leg 12 of a user so that the tubular member 36 is located at the front of the leg and centered below the kneecap. The straps 18 and 20 are then manipulated to supply a desired degree of compression of the sleeve 16 around the leg 12 of the user. For example, with reference to FIGS. 3–6, the foot and leg 12 of the user is passed through the sleeve 16 and the sleeve pulled upwardly to a location just below the kneecap 14. The seam 30 is generally oriented at the back center of the leg and the midpoint of the tubular member 36 at the front center of the leg 12, which is generally across the patellar tendon. As seen in FIG. 3, the contoured portion of the device 10 adjacent the seam 30 is preferably positioned to fit comfortably just below the back of the knee 14 and the ends 52 and 62 of the straps 18 and 20 are passed through the apertures in the D-rings 44 and 48 of the strap closure members 22 and 24, respectively.

Figure 4:
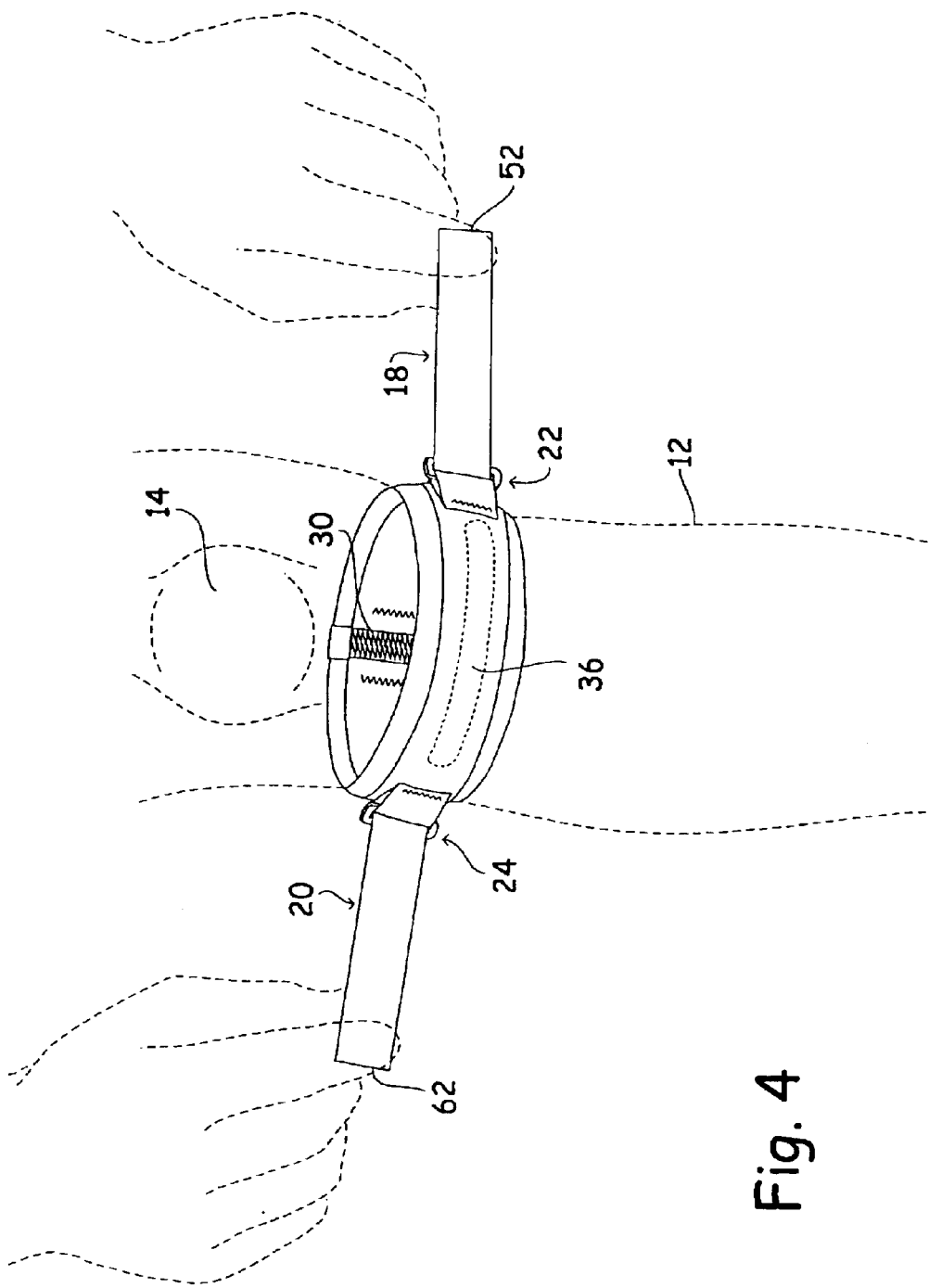
Figure 5:
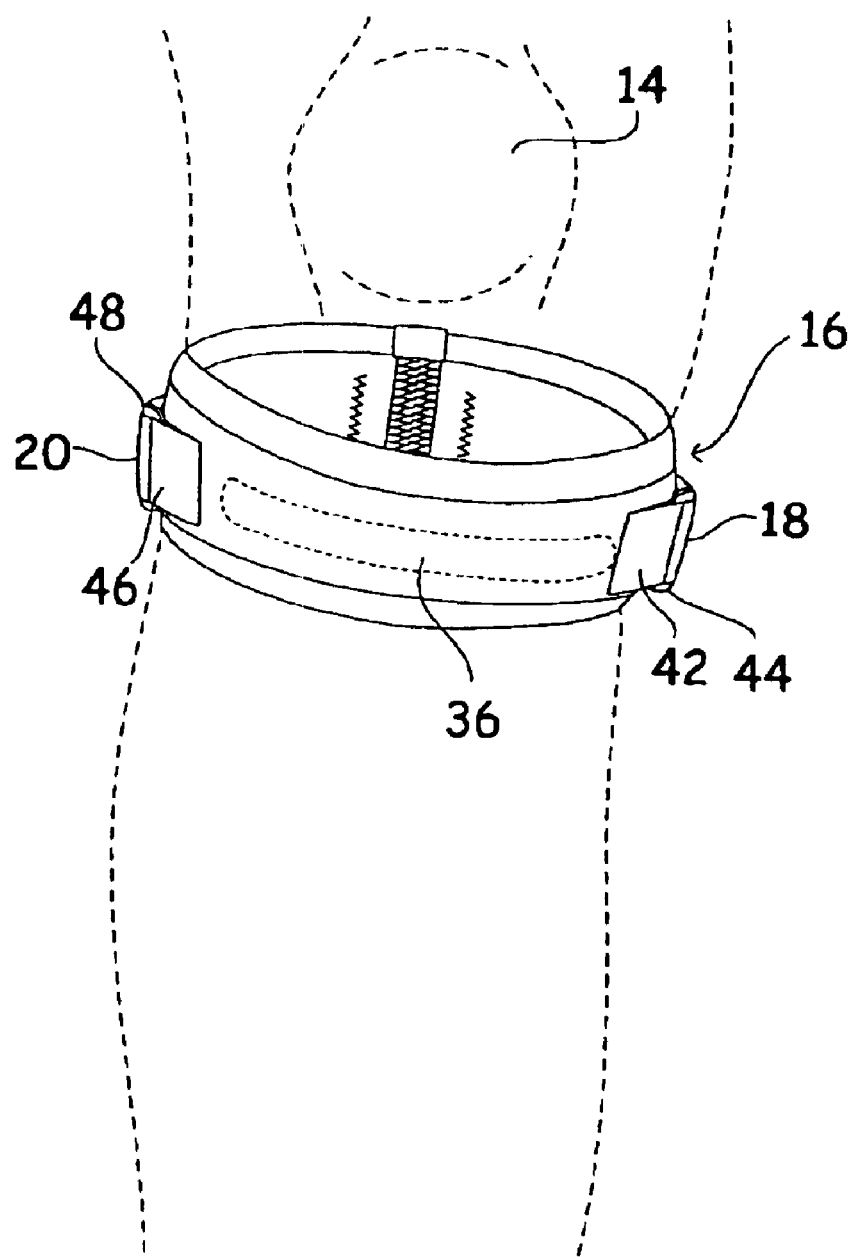
Figure 6:
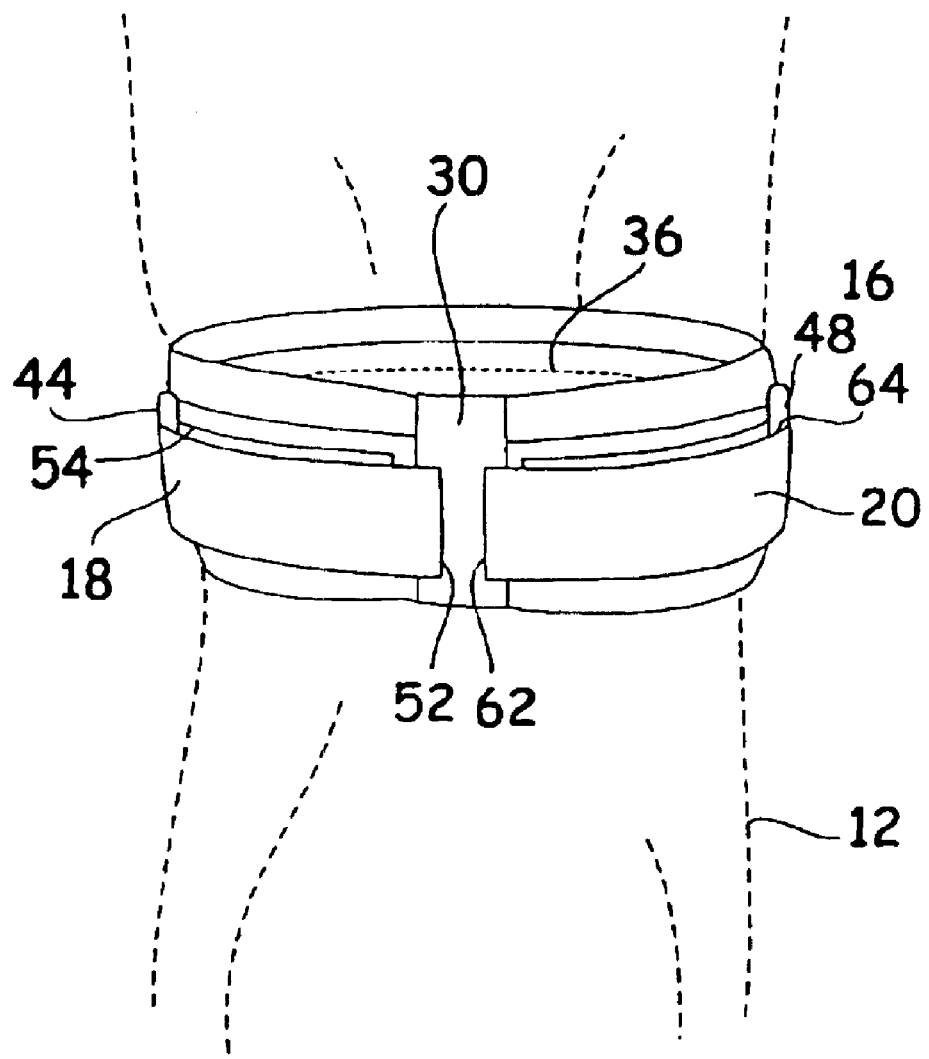

Next, with reference to FIG. 4, the user grasps the ends 52 and 62 of the straps 18 and 20 and pulls the straps 18 and 20 by applying a desired amount of force. Then, as seen in FIGS. 5 and 6, the straps 18 and 20 are folded back to secure the hook material 56 to the loop material 54, and the hook material 66 to the loop material 64. This maintains the straps 18 and 20 in the desired tensioned states, with the tubular member 36 applying force to the patellar tendon.

It is believed that use of the device 10 as described herein provides support, compression, and warmth to the patellar tendon and thus may be useful to provide a treatment for pain associated with patellar tendonitis and/or other musculotendinous conditions of the knee.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A device for providing support, compression, and warmth to the patellar tendon of a knee, the device comprising an elastic sleeve having a circumferential length and opposite interior and exterior surfaces; a compressible tubular member having first and second opposite ends and secured along the circumferential length of the sleeve; first and second steps secured adjacent the exterior of the sleeve and generally diametrically across the sleeve from the tubular member, the first strap having a hook surface and an adjacent loop surface and being secured adjacent the exterior surface of the sleeve at a first attachment point and the second strap having a hook surface and an adjacent loop surface and being secured adjacent the exterior surface of the sleeve at a second attachment point located generally adjacent to the first attachment point so that the first and second straps may be positioned to extend in generally opposite directions around the exterior circumference of the sleeve, a first strap closure member secured adjacent the exterior surface of the sleeve and positioned between the first attachment point and the first end of the tubular member; and a second strap closure member secured adjacent the exterior surface of the sleeve and positioned between the second attachment point and the second end of the tubular member, wherein the device is positionable on the knee so that the tubular member is generally oriented across a front portion of the knee adjacent the patellar tendon and the device may be tensioned to provide compression and support to the patellar tendon by (1) exerting a first force on the first strap and passing the first strap through the first strip closure member and folding the first strap back to secure the book material and the loop material of the first strap together to maintain application of the first force and (2) exerting a second force on the second strap and passing the second strap through the second strap closure member and folding the second strap back to secure the hook material and the loop material of the second strap together to maintain application of the second force.

2. The device of claim 1, wherein the sleeve comprises a length of elastic fabric material having the ends sewn together to form seam, with the portion of the sleeve adjacent the seam contoured to fit comfortably below the back of the knee.

3. The device of claim 1, wherein the first and second strap closure members each comprise a length of fabric material having the ends thereof attached to sleeve to form a loop and a D-ring encircled by the loop.

4. The device of claim 1, wherein the sleeve has a circumference in an unstretched state of from about 3 to about 4 inches less than the circumference of the knee of the user on which the device is to be positioned.

* * * * *